United States Patent [19]

Eriksson et al.

[11] Patent Number: 5,423,778
[45] Date of Patent: Jun. 13, 1995

[54] SYSTEM AND METHOD FOR TRANSPLANTATION OF CELLS

[75] Inventors: Elof Eriksson, 5 Lanark Rd., Wellesley Hills, Mass. 02181; Peter M. Vogt, Newton, Mass.

[73] Assignee: Elof Eriksson, Wellesley Hills, Mass.

[21] Appl. No.: 897,357

[22] Filed: Jun. 11, 1992

Related U.S. Application Data

[63] Continuation-in-part of Ser. No. 707,248, May 22, 1991, Pat. No. 5,152,757, which is a continuation of Ser. No. 451,957, Dec. 14, 1989, abandoned.

[51] Int. Cl.$^6$ .............................................. A61F 13/00
[52] U.S. Cl. ................................. 604/305; 604/891.1; 435/240.1
[58] Field of Search ............................... 604/304–308, 604/890.1, 891.1; 623/15; 424/DIG. 13, 574, 422, 423; 128/888; 435/41, 172.1, 240.1, 240.2, 240.21, 240.23, 240.31, 240.241, 240.243, 287, 289

[56] References Cited

U.S. PATENT DOCUMENTS

| | | |
|---|---|---|
| 3,026,874 | 3/1962 | Stevens . |
| 3,288,140 | 11/1966 | McCarthy . |
| 3,367,332 | 2/1968 | Groves . |
| 3,580,254 | 3/1971 | Stuart . |
| 3,814,097 | 6/1974 | Ganderton et al. . |
| 4,304,866 | 12/1981 | Green et al. .................... 435/240.23 |
| 4,347,841 | 9/1982 | Benyó et al. ......................... 602/48 |
| 4,767,746 | 8/1988 | Catsimpoolas et al. . |
| 4,788,971 | 12/1988 | Quisno . |
| 4,868,116 | 9/1989 | Morgan et al. .................. 435/240.2 |
| 4,888,291 | 12/1989 | Barrandon et al. ........... 435/240.241 |
| 4,980,286 | 12/1990 | Morgan et al. . |
| 5,175,092 | 12/1992 | Gabriels, Jr. ........................ 435/29 |
| 5,201,728 | 4/1993 | Giampapa ........................ 604/891.1 |

FOREIGN PATENT DOCUMENTS

| | | |
|---|---|---|
| 641061 | 8/1950 | United Kingdom . |
| WO87/00201 | 1/1987 | WIPO . |
| WO91/08793 | 6/1991 | WIPO . |
| WO92/15676 | 9/1992 | WIPO . |

OTHER PUBLICATIONS

Jonathan A. Garlick et al., "Retrovirus-Mediated Transduction of Cultured Epidermal Keratinocytes", The Society of Investigative Dermatology, Inc., vol. 97, No. 5, Nov. 1991, pp. 824–829.

Jeffrey R. Morgan et al., "Expression of an Exogenous Growth Hormone Gene by Transplantable Human Epidermal Cells", Science, vol. 237, Sep. 1987, pp. 1476–1479.

James M. Wilson et al., "Implantation of Vascular Grafts Lined with Genetically Modified Endothelial Cells", Science, vol. 244, Jun. 1989, pp. 1344–1346.

(List continued on next page.)

Primary Examiner—C. Fred Rosenbaum
Assistant Examiner—V. Alexander
Attorney, Agent, or Firm—Quarles & Brady

[57] ABSTRACT

Gene transfer of genetic material with viral vectors or plasmid, in combination with a wound treatment chamber, into keratinocytes, especially those including a high percentage of epidermal stem cells, has been demonstrated to be particularly effective as a means of implanting genetically engineered cells and obtaining long term survival. By employing the wound chamber system, direct in vivo gene transfer can also be done to exposed cells in an open wound. Skin stem cells which are located in the hair follicles are used to greatly enhance long term survival. The use of the wound chamber system for gene transfer also allows non-invasive assessment of the success of transfer by assaying for the presence of the expressed protein in wound fluid, in contrast to the prior art use of invasive techniques, such as biopsies, in order to achieve the same assessment of early expression. A wide variety of proteins and materials can be expressed, either for secretion into the general blood and lymphatic system, or to alter the properties of the protein, for example, to not express proteins eliciting an immune response against the transplanted cell.

22 Claims, 4 Drawing Sheets

Conceptional partial thickness wound model for in-vivo gene transfer

Exposed undersurface of partial thickness skin flap

Exposed hairfollicle

OTHER PUBLICATIONS

Theodor Kaufman et al, "Topical oxygen and burn wound healing: a review", Burns, vol. 9, No. 3, pp. 169–173.

James G. Rheinwald et al., "Epidermal Keratinocytes: the Formation of Keratinizing Colonies from Single Cells", Cell, pp. 331–343.

Phyllis C. Wright, "Fundamentals of Acute Burn Care and Physical Therapy Management", Physical Therapy, vol. 64, No. 8, Aug. 1984, pp. 1217–1231.

Kazumiko Juni et al., "Controlled Drug Permeation. II. Comparative Permeability and Stability of Butamben and Benzocaine", Chem. Pharm. Bull., vol. 25, 1977, pp. 1098–1100.

Amitav Majumdar et al., "Diffusion of Local Anesthetics Through Liquid Membranes", Elsevier Science Publishers B.V., 1986, pp. 329–339.

Karl Breuing, M.D., "Healing of Partial Thickness Procine Skin Wounds in a Liquid Environment", Journal of Surgical REsearch, vol. 52, No. 1, Jan. 1992, pp. 50–58.

Elof Eriksson et al., "In Vivo Cell Culture Accelerates Reepithelialization", Surgical Forum, vol. 42, No. 0, 1991, pp. 670–673.

Elizabeth S. Fenjves et al., "Systemic distribution of apolipoprotein E secreted by grafts of epidermal keratinocytes: Implications for epidermal function and gene therapy", Proceedings of the National Academy of Sciences of the USA, vol. 86, No. 22, Nov. 1989, pp. 8803–8807.

SYSTEM AND METHOD FOR TRANSPLANTATION OF CELLS

This is a continuation-in-part of U.S. Ser. No. 07/707,248 entitled "System for Diagnosis and Treatment of Wounds" filed May 22, 1991, now U.S. Pat. No. 5,152,757 by Elof Eriksson, which is a continuation of U.S. Ser. No. 07/451,957 filed Dec. 14, 1989, now abandoned.

BACKGROUND OF THE INVENTION

The invention relates to a system for culture and transplantation of normal and genetically engineered cells onto a patient.

Keratinocytes are the principle cells which cover the surface of the body. They are capable of producing proteins, particularly keratin, which constitutes the main surface barrier of the body. For several different reasons, keratinocytes are attractive potential targets for gene transfer. Since they are located on the surface of the body, they are easily accessed both for gene manipulation and monitoring. If complications from gene transfer would occur, for instance, the development of local tumors or local infections, these could more easily be treated in the skin than elsewhere.

To date, genetic manipulation of keratinocytes has been done in one principle way. Skin has been harvested, the keratinocytes have been separated from the fibroblasts, and then the keratinocytes individually isolated and brought into suspension. These suspensions of keratinocytes have then been cultured to confluence using tissue culture techniques, as reported by Rheinwald, J. G., Green, H. Serial Cultivation of Human Epidermal Keratinocytes: The Formation of Keratinizing Colonies From Cells. *Cell* G, 331–343, 1975.

The new genetic material has been introduced into the keratinocyte while being grown in vitro using either a viral vector or plasmid, as reported by Morgan, J. R., Barrandon, Y., Green, H., Mulligan, R. C. Expression of an Exogenous Growth Hormone Glue by Transplantable Human Epidermal Cells. *Science*, Vol. 237, 1476–1479 (1987) and Tenmer, J., Lindahl, A., Green, H. Human Growth Hormone in the Blood of Athymic Mice Grafted With Cultures of Hormone-Secreting Human Keratinocytes. *FASEB J.*, 4:3245–3250 (1990). The transfected cells are then usually resuspended and grown on selective media in order to increase the yield of transfection. Sheets of keratinocytes are then transplanted back to the mammal from which the keratinocytes were harvested.

Even though the in vitro yield has been acceptable, the in vivo yield has been unacceptably low, both short and long term. It has been very difficult to document any significant long term (more than thirty days) expression with these techniques, for example, as reported by Garlick, J. A., Katz, A. B., Fenvjes Esitaichman, L. B. Retrovirus Mediated Transduction of Cultured Epidermal Keratinocytes. *J. Invest, Dermatol.*, 97:824–829, 1991.

It is therefore an object of the invention to provide an improved method for transplanting cells into a patient, especially keratinocytes and genetically engineered cells.

It is a further object of the present invention to provide a means for transplantation which is economical, practical, readily manufactured and can be customized to the patient with minimal effort and expense.

SUMMARY OF THE INVENTION

Gene transfer of genetic material with viral vectors, plasmids, or gene guns into keratinocytes, especially those including a high percentage of epidermal stem cells, in combination with the use of an "in vivo" culture chamber has been demonstrated to be particularly effective for culture keratinocytes.

By employing the wound chamber system, direct in vivo gene transfer can be done to exposed cells in an open wound. If these cells were not covered by the chamber, they would desiccate and die. The chamber also completely seals the wound from the outside, eliminating the spread of genetic material and vectors to places outside of the wound. At the same time, the chamber prevents the accidental introduction of undesired contamination, including viruses and other microorganisms and chemical contaminants into the wound.

Skin stem cells which are located in the hair follicles and in the basal layer of the skin are used to greatly enhance long term survival. Other cells, especially keratinocytes, can be used, alone or in combination with the stem cells.

The use of the wound chamber system for gene transfer also allows non-invasive assessment of the success of transfer by assaying for the presence of the expressed protein in wound fluid, in contrast to the prior art use of invasive techniques, such as biopsies, in order to achieve the same assessment of early expression.

A wide variety of proteins and materials can be expressed, either for secretion into the general blood and lymphatic system, or to alter the properties of the protein, for example, to not express proteins eliciting an immune response against the transplanted cell.

DETAILED DESCRIPTION OF THE INVENTION

U.S. Ser. No. 07/707,248, now U.S. Pat. No. 5,152,757 describes a treatment system for wounds and other skin disorders including a chamber securable about the periphery of a wound, having portal means for introduction into and removal of treatment fluids from the chamber, treatment fluid, at least one treatment additive, control means for treatment variables, and monitoring means for monitoring wound conditions. Treatment fluid and additives are selected according to wound indications and include growth factors, antibiotics, anesthetics, enzymes and oxygen. Treatment variables such as temperature, colloid osmotic pressure, pH, ion concentration and oxygen content are controlled according to wound indications.

The chamber is secured about the periphery of a wound, a treatment fluid and at least one treatment additive introduced into the chamber, and the treatment variables controlled according to wound conditions. Examples of disorders that can be treated include wounds such as burns, pain, tumors, and infections. The chamber can also be used to culture cells onto wounds, where the dispersed cells are introduced into the chamber and allowed to settle and grow at a wound site.

The method described herein is based on two principle components. One is the targeting of epidermal stem cells for gene transfer. The second is the use of the wound chamber in order to create an in vivo tissue culture environment, which eliminates the need to culture cells in vitro when introducing the genetic material into the cells.

Epidermis keratinocytes are ideally suited for gene transfer and recombinant DNA expression in epidermal wound healing because of their key functions in mechanical stability and integrity and in secretion of biologically active substances, such as apolipoprotein A, which are detectable in the systemic blood circulation. It has been demonstrated that suspensions of genetically engineered keratinocytes can be transplanted onto open wounds, which eliminates the need to grow them into sheets. This makes the process of gene transfer in keratinocytes much easier and less time consuming.

Cells.

Keratinocytes are separated from the dermis with dispase and then individually separated with trypsin and the fibroblasts removed. By targeting keratinocytes in the hair follicles, which provide a high number of stem cells, it has been found both that the yield of transfection is higher and that these cells are stably incorporated into the basal layer of the epidermis. The cells of the hair follicles serve as "stem cells of the epidermis". By using mechanical separation of the rest of the epidermis from this area these cells can either he removed using a dermatome technique or the genetic material can he directly introduced into these cells in situ.

Cells can be obtained as needed from other sites on the patient, including other tissues, for instance, bone marrow cells, muscle cells, and cells; from endocrine organs.

Introduction of Genetic Material

Genetic material can be introduced into the cells with plasmid, retroviral, or gene gun transfer using standard techniques. The genetic material would encode proteins such as growth factors, hormones, and other therapeutic proteins. These would speed the healing of wounds and correct certain deficiencies, such as parathyroid, growth hormone, and other hormone deficiencies, as well as deficiencies of certain clotting factors such as factor VIII. Cells can also be engineered to not express a protein, such as a protein involved in an immune response, for example, a human leukocyte antigen (HLA).

Keratinocytes are harvested and brought into suspension through exposure to enzymes, first to dispase and then trypsin, then grown to subconfluence in an incubator. Recombinant DNA is then introduced into the cell using a viral vector, plasmid or gene gun technique. After this the keratinocytes are suspended and injected into full thickness wounds which are covered by a wound chamber. These keratinocytes will not only survive, but will show continued presence of cells expressing the marker gene in the basal layer of the epidermis.

The keratinocytes and fibroblasts in the wound can be made to produce, for instance, growth factors, if the gene encoding the growth factor is introduced into the genome or cytoplasm of these cells. The expressed growth factor will then not only speed the healing of the wound, but also help to heal wounds that would not heal otherwise.

The following protocol is utilized for direct in vivo gene transfer in order to achieve systemic expression of the transferred gene.

Figure 1:
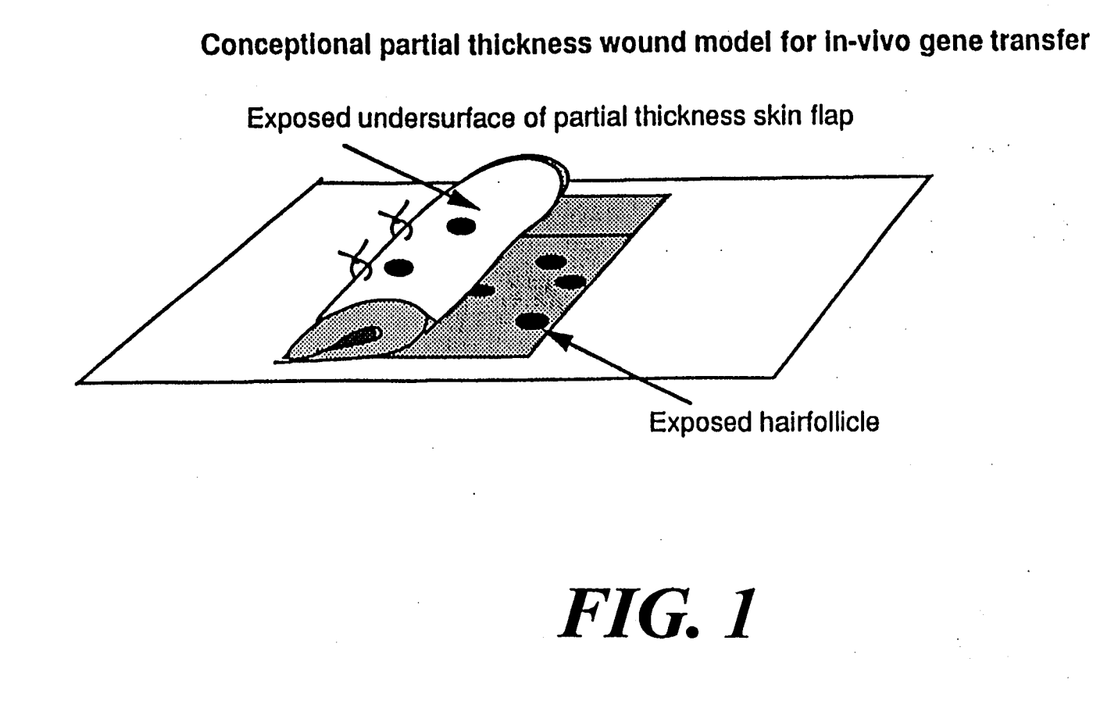
FIG. 1 is a schematic of the exposed undersurface of a partial thickness skin flap used to expose hair follicles to obtain epidermal stem cells.

Stem cells located in the hair follicles deep to the epidermal dermal junction are exposed by creating a flap of epidermis where the deep portion of the flap contains the basal layer of the epidermis. The exposed wound surface contains the portion of the hair follicles with the stem cell keratinocytes. The genetic material is then introduced with a gene gun (ACCELL ™, Dr. Dennis McCabe 1986) and then covered in a wound chamber. Alternatively, the wound with the exposed undersurface of the flap (see FIG. 1) is exposed in the wound chamber and the gene in an appropriate vector for viral transfer or plasmid transfer is introduced into the chamber. Early expression of the gene is assayed in samples of this chamber fluid at 24 and 48 hours. After this the epidermal flap is sutured back in place and the wound is sealed with a dressing.

The Chamber

In the preferred embodiment, cells are cultured in a system including a chamber, treatment fluid (which may be nutrient media, physiological saline, or some other compatible solution), treatment additives (such as antibiotics and buffering agents), means for controlling treatment variables and means for monitoring cell growth.

The wound chamber, which is made of vinyl or other flexible transparent material, such as polyurethane, has a bellows shape and an opening which corresponds to the size of the wound, either the chronic wound or a superficial wound created specifically for the purpose of gene transfer. The chamber contains a small amount of normal saline with antimicrobial agents. When plasmid or retroviral vectors are used, the chambers are simply attached over the wound and the vector is injected into the chamber and the chamber is then resealed. When the gene gun is used, the DNA is delivered into the cell and the chamber with normal saline and antibiotics is then attached to the perimeter of the wound. Wound fluid is sampled in order to assay expression of the secretable gene product (growth factor) at 24 and 48 hours. The wound is treated in the chamber until healed.

The chamber encloses a predetermined surface area about the culture site. The chamber provides protection for the wound from the surrounding non-sterile environment, control of treatment variables, containment for continuous fluid treatment, an effective delivery system for additives, direct monitoring of cell growth. Monitoring can be accomplished visually if the chamber is formed of a transparent material, or by extraction and analysis of fluid from the chamber. Fluid extracted from the system can be analyzed for factors which provide an indication of the status of healing, as well as the presence of undesirable components such as microorganisms, low oxygen, high carbon dioxide and adverse pH. The fluid may be tested for the number and type of bacteria and other microorganisms, the number and type of cells, the amount and type of proteins secreted by the patient and the cells within the chamber, and other factors such as drug levels, oxygen, carbon dioxide and pH.

The treatment system provides control over variables including temperature, specific ion concentration, colloid osmotic pressure, glucose concentration, amino acid content, fat concentration, oxygen concentration and carbon dioxide concentration and pH.

Portal means provide access for the introduction of treatment fluids and treatment additives into the chamber and extraction of fluid from the chamber. In some embodiments such as that shown in FIG. 2, treatment fluid is introduced into the chamber by injection with a conventional hypodermic syringe through the wall of the chamber, preferably made of a flexible, self-repairing plastic. In other embodiments such as that shown in FIG. 3, the chamber has an inlet and outlet port or separate inlet and outlet ports. Valve mechanisms are necessary where the apparatus is not to be connected to a treatment fluid reservoir and a drain or connected to a continuous perfusion system. The seals of the ports would be broken at an appropriate time for connection to other apparatus, such as a continuous perfusion system, at a hospital for example.

A preferred embodiment of the treatment system incorporates continuous perfusion of treatment fluid through inlet and outlet ports. A pump or gravity may be used to move the treatment fluid. The treatment fluid may be recirculated after filtering and other appropriate action (eg. heating or cooling). Alternately, fresh treatment fluid may be introduced and contaminated fluid disposed of. In an embodiment described in U.S. Ser. No. 07/707248, now U.S. Pat. No. 5,152,757 the chamber contains a reservoir or more than one chamber, with the additional chamber serving as a source of fresh culture media, oxygen, and treatment additives.

Figure 2A:
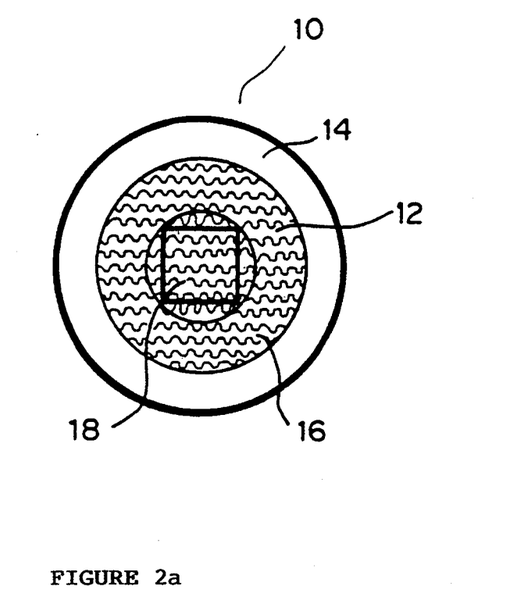
FIG. 2a is a top view of a preferred embodiment of a chamber for culturing keratinocytes on a patient.
Figure 2B:
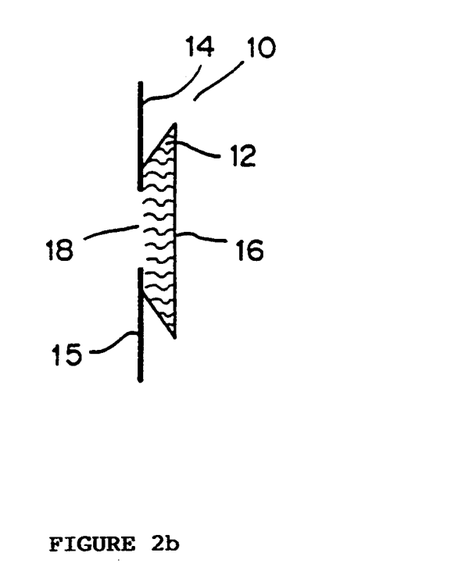
FIG. 2b is a side view of a preferred embodiment of the chamber.

FIG. 2a and b show a preferred embodiment of a chamber 10, FIG. 2a is a top view and FIG. 2b is a side view. The chamber 10 has a bellows-type construction that prevents the majority of the chamber from contacting the wound service and in fact acts to push the chamber away from the wound. The chamber 10 is preferably constructed of clear vinyl or other sterilizable, flexible, heat-sealable, gas and moisture impermeable material. The bellows fold 12 allows for a large capacity for treatment fluid as well as ease of construction. For construction, an annular base 14 is heat or ultrasound welded to an annular bellows fold 12 piece and a circular top 16 welded to bellows fold 12 piece. Circular top 16 is a substantially transparent material. The remaining components are not necessarily transparent but may be. A transparent annular base may provide easy visual inspection for leakage. An opening 18 in annular base 14 is provided that corresponds in size to the wound or site for transplantation. The bottom side 15 of annular base 14 is provided with an adhesive tape or coating suitable for securing the chamber to skin.

As those skilled in the art will readily recognize, a removable sheet for protecting the adhesive and maintaining the sterility of the interior of the chamber is desirable. The chambers may be stored in a sterile pack for years. This chamber can take many shapes in order to fit wounds from the size of one square centimeter up to the size of a whole extremity. It is important that the adhesive surface be sufficient to secure the bandage to the skin surface to ensure a leak-proof seal.

As previously mentioned, treatment fluid and treatment additive introduction and subsequent extraction may be accomplished directly through the chamber walls by a needle and syringe. A self-repairing material to construct chamber 10 is contemplated. An alternative method would be to use inlet and outlet ports allowing the introduction and extraction of various substances into the chamber.

Figure 3:
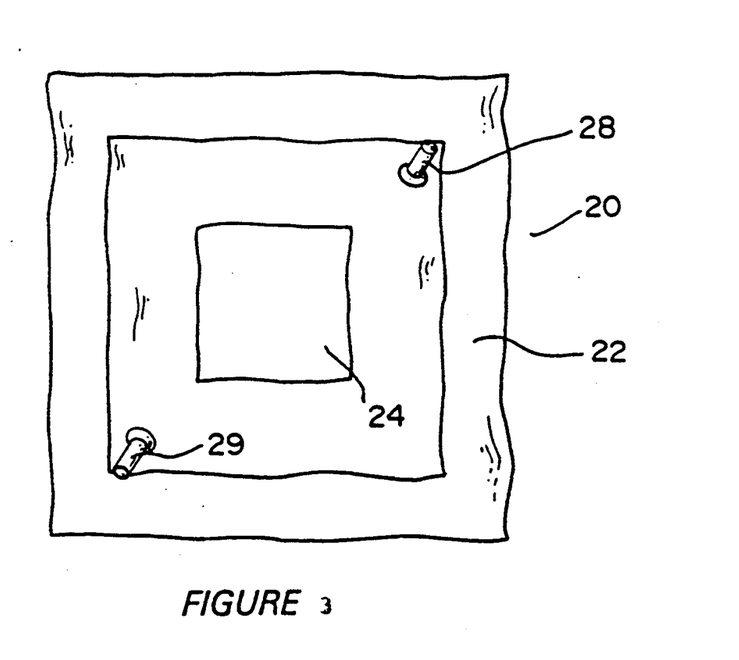
FIG. 3 is a prospective view of a ported embodiment of a chamber for culturing keratinocytes.

FIG. 3 is a view of a chamber 20 for enclosing a predetermined surface area about a site on a patient where cells are to be cultured, where the chamber is open to the skin 24 and sealed at the edges 22 to the skin surface about the wound by means of an adhesive. The chamber 20 has a transparent section 24 for visual wound monitoring, a portal means 28, 29 for introduction of treatment fluid and treatment additives into the chamber and extraction of fluid from the protective chamber, and monitoring means (not shown) for analyzing extracted fluid for predetermined variables and wound conditions.

Preparation of site for culturing cells.

The site for culturing cells is prepared by removing infected or burned skin, if necessary, or by creating an appropriate wound for transplantation of engineered cells. The skin adjacent to the wound is then cleaned so that there will be good adhesion between the chamber and the skin. The open portion of the chamber is then placed over the site, with the adhesive edges securing the chamber to the skin, then an appropriate culture medium and cells are introduced into the sealed chamber. The treatment fluid may be introduced and then extracted in favor of fresh culture media in a continuous or batch process. Selected treatment additives may be introduced into the chamber continuously or at a predetermined time or at periodic intervals. Appropriate control of treatment variables is also effected. Monitoring is accomplished by examination of the patient and visual examination of the fluid within the chamber and the wound itself. In addition, samples of fluid are extracted from the chamber for analysis and diagnosis. The chamber is removed once sufficient healing of the wound has occurred.

For example, to determine whether or not the wound is healed, the protein content of the extracted fluid is analyzed. When the protein content of the extracted fluid decreases to the level present in chambers containing fluid that are placed over normal skin, the wound is healed. Methods for determining protein content is well known in the art and are inexpensive and fast. The types of protein and the relative amounts of the types of protein can also be determined to further evaluate healing and expression of exogenous genetic material.

Control of Treatment or Culture variables.

Treatment of each patient is specific for the conditions within the chamber. Control over treatment variables can include continuous cooling to 34° C. for the first 24 hours. Monitoring can include analyzing extracted fluid for protein and microorganisms, with samples extracted every 24 hours. For example, when the number of microorganisms is less than 10 to the 4th per milliliter or per cc, infection has been resolved. Protein levels checked every day should be less than 24 mg/dl/cm$^2$.

As noted above, there are a number of treatment variables which may be controlled by the system. One such treatment variable which may be controlled is temperature. It has been found that heating the wound from a temperature of approximately 27° C. (a common temperature of a lower extremity wound) to 37° C. accelerates wound healing. Experimental data has shown that at a wound temperature of approximately 37° C., the rate of wound healing is more than twice as fast as at a temperature of 27° C. The temperature of the wound area can be achieved by heating the treatment fluid. Cooling has also been proven beneficial in the case of acute burn and other traumatic wounds. Cooling reduces pain, swelling and destruction of tissue. In general terms, acute wounds benefit from cooling during the first hours after occurrence of the wound and later, wounds benefit from a temperature of approximately 37° C. Cooling can similarly be effected by cooling the treatment fluid.

Other treatment variables may also be optimized. For example, ion concentrations should be kept close to extracellular ion levels. Glucose, amino acid and fat concentrations should be kept close to the concentrations present in plasma or corresponding to a skin tissue culture medium. Oxygen and carbon dioxide concentrations should also be maintained at their normal tissue levels. Oxygen is an important treatment additive, and is essential for cell growth.

Treatment additives and Culture Media.

Normal or physiological buffered saline is the basic culture media. Buffering agents, anesthetics such as lidocaine, antibiotics such as penicillin or streptomycin, chemotherapeutic agents, and growth factors including epidermal growth factor (EGF), platelet-derived growth factor (PDGF), insulin-like growth factor (IGF), basic fibroblast growth factor (bFGF), and cholera toxin (CT) can be added to the culture/treatment media. Tissue culture mediums and fluids which increase osmotic pressure and oxygen accessibility may also be introduced to the chamber as treatment additives.

Selection of treatment additives is wound specific. For example, if an infection has been diagnosed, antibiotics are added in the amount of one single parenteral dose per 1,000 cc of fluid. Furthermore, a treatment additive of gentamicin, tobramycin or carbenicillin is appropriate for a wound infection with Pseudomonas, detected by analyzing extracted fluid. When hypoxia has been diagnosed, the liquid is passed through an oxygenating chamber before entering the chamber. If a tumor has been diagnosed, chemotherapy is given in an amount of one single parenteral dose per 1,000 cc of fluid. In situations involving a wound containing necrotic tissue and debris, proteolytic enzyme is added to the liquid. Immune modulators are added to the treatment fluid if an inflammatory reaction is exhibited. Epidermal growth factor is added in a concentration of 10 nanograms per cc when required.

The present invention will be further understood be reference to the following non-limiting examples.

EXAMPLE 1

Transfection of keratinocytes and expression of human growth hormone in culture and following transplantation into partial thickness wounds.

In the first series of experiments, keratinocytes were harvested, plated in culture flasks, land transfected with a viral vector technique, using the method of Wilson, J. M, Biriuyi, L. U., Salomon, R. U., et al. Transplantation of Vascular Grafts Lined With Genetically Modified Endothelial Cells. *Science,* 244:1344–1346 (1980), or a plasmid transfer technique, as described by Felgner, P. L., Galik, T. R., Holmer, et al. Lipofection: A Efficient, Lipid Mediated DNA-Transfection Procedures. *Proc. Natl. Acad. Sci.,* 84:7413–7417 (1987), the teachings of which are incorporated herein.

Specifically, keratinocytes were harvested from two female Yorkshire pigs by partial thickness skin excision, dispase separation of epidermis (0.25% Dispase, 2–3 h at 37° C.) trypsinization (0.1% Trypsin, 0.02% EDTA, 30 min at 37° C.) and mincing to a single cell suspension. They were grown to subconfluence (60–70%) and incubated with a replication defective murine Moloney leukemia retroviral vector. The DNA sequence for hGH was inserted into the viral genome and was under the promoter control of the viral long-terminal repeats (LTR's). The infected keratinocytes were trypsinized, resuspended in saline containing penicillin (100 U/ml) and streptomycin (100 μg/ml). They were transplanted to full thickness wounds created on the dorsum (n=10) in an autologous fashion. Full thickness wounds seeded with unmodified keratinocytes (n=10) and saline (n=10) served as controls. All wounds were covered with sterile vinyl chambers for maintenance of a liquid wound environment throughout the study. The presence of hGH in the culture medium or the wound fluid was determined by radioimmunoassay.

The same methodology was used with the Lac Z gene, an intracellular marker gene.

Figure 4:
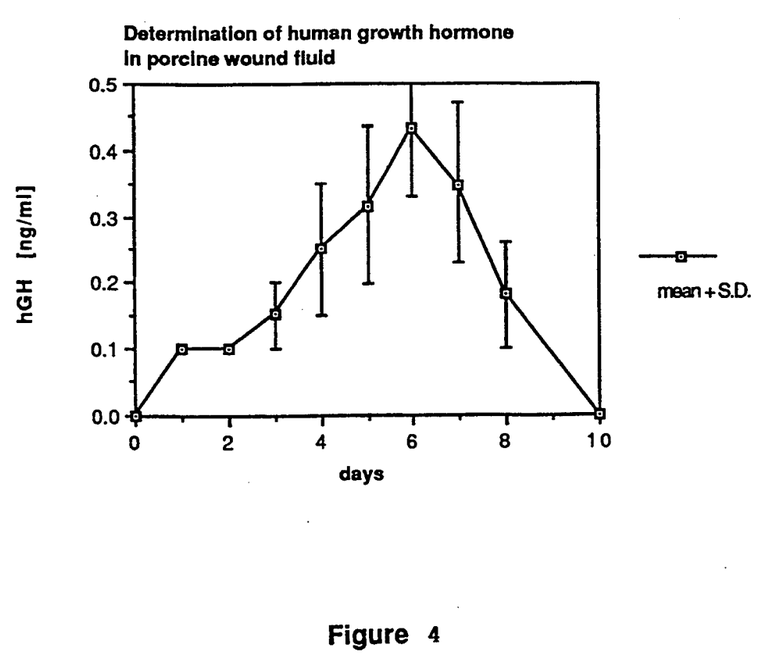
FIG. 4 is a graph showing expression of the gene encoding human growth hormone in keratinocytes, ng/ml versus time in days.
Figure 5A:
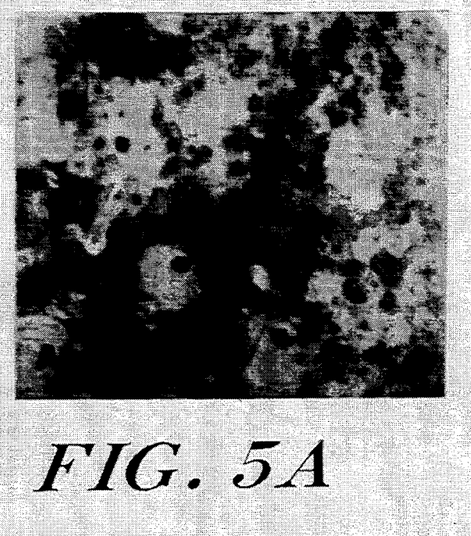
FIG. 5a is a photograph of high frequency transfection with lacZ gene, $\beta$-Gal positive cells, of primary pig keratinocytes by retroviral gene transfer.
Figure 5B:
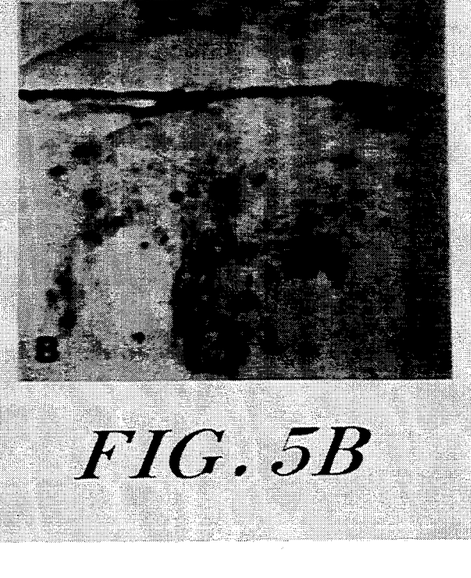
FIG. 5b is a photograph of expression of the lacZ gene in regenerated epithelium of a full thickness wound reconstituted by retrovirally transfected transplanted keratinocytes, $\beta$-Gal staining.

Significant expression of both genes in this system was obtained, as shown by FIGS. 4 and 5a and b. Histologic sections of the skin showed that the keratinocytes that had the Lac Z marker gene were not stably incorporated into the basal layer, but migrated to the surface and were lost into the stratum corneum. When analyzing the reasons behind this, it was concluded that the dispase separation of dermis from epidermis did not allow for harvesting of a sufficient amount of stem cells. An additional reason was that the repeated trauma of harvesting the cells, exposure to tissue culture medium with relatively high calcium, and the cellular injury from the virus or the plasmid medium, caused a near terminal differentiation of the keratinocytes. Accordingly, results were greatly improved by using a higher percentage of epidermal stem cells obtained from the hair follicles, and decreasing the exposure to calcium and viral or bacterial medium.

In vitro (culture medium) hGH was detected on day 4 after retroviral transfection with a mean daily production of 2.0 ng/ml. In vivo (wound fluid) hGH production was first detected 24 hours after transplantation (0.1 ng/ml) peaked at 132 h (0.42 ng/ml) and returned to baseline by day 10. Healing times, assessed by the protein efflux assay in wound fluid, wounds receiving hGH-keratinocytes (12.1±1.0 days) were no different than those of wound receiving non-infected keratinocytes but significantly shorter ($p<0.005$) than non-transplanted control wounds (14.7±0.6 days). Histologically transplanted keratinocytes established a multilayer epithelium as early as day 6 (saline treated controls by day 11).

The results demonstrate that autologous keratinocytes carrying the hGH gene will continue to express the hGH gene when transplanted to full thickness wounds. The produced hGH does not influence healing times. Compared to the in vitro keratinocyte cultures hGH production in vivo is regulated in a time dependent fashion. This may be either due to a regulation of hGH gene expression by keratinocytes during epithelialization, loss of hGH producing keratinocytes due to terminal differentiation, or antibody reaction to the foreign protein, as discussed by Selden, et al., "Human Growth Hormone as a Reporter Gene in Regulation Studies Employing Transient Gene Expression" *Mol. Cell Biol.* 6(9):3173–3179 (1986). Since genetically engineered keratinocytes not only improve reepithelialization of full thickness wounds but also release a recombinant DNA product during healing they may provide a new way of delivering and expressing therapeutic peptides, like growth factors, in wound healing. By using a topical chamber system, direct application of genetically engineered cells and monitoring of the gene product can easily be facilitated.

Modifications and variations of the present invention, a method for transplanting cells, especially genetically engineered keratinocytes and epidermal skin cells, will be obvious to those skilled in the art. Such modifications and variations are intended to come within the scope of the appended claims.

We claim:

1. A method for culturing cells at a site on and within a patient comprising attaching to the surface of the patient and at the site on a patient where cells are to be grown a chamber formed of a flexible, moisture and gas impermeable material containing a fluid medium suitable for culturing of cells and open to the patient so that the medium is in contact with the patient.

2. The method of claim 1 further comprising adding cells to be cultured into the chamber.

3. The method of claim 2 wherein the cells are selected from the group consisting of keratinocytes and epidermal stem cells.

4. The method of claim 3 wherein the epidermal stem cells are isolated by removing the cells from hair follicles on the underside of partial thickness skin flaps.

5. The method of claim 2 wherein the cells are engineered to express exogenous genetic material.

6. The method of claim 5 wherein the cells are engineered to express proteins selected from the group consisting of hormones, immunomodulators, clotting factors, antigens, and antibodies.

7. The method of claim 2 wherein the cells are engineered to not express proteins eliciting an immune reaction against the cells.

8. The method of claim 7 wherein the cells do not express HLA antigens.

9. The method of claim 2 further comprising introducing exogenous genetic material into the cells in the chamber.

10. The method of claim 1 further comprising controlling culture variables in the chamber.

11. The method of claim 10 wherein the variables are selected from the group consisting of pH, gas concentrations, ion concentrations, and temperature.

12. The method of claim 1 further comprising adding compounds to the chamber selected from the group consisting of antibiotics, anesthetics, chemotherapeutic agents, immunomodulators, and growth factors.

13. A method for increasing the yield of genetically engineered cells in a patient comprising the steps of selecting in vivo epidermal stem cells as the cells to be engineered and introducing genetic material into said epidermal stem cells.

14. The method of claim 13 further comprising selecting the cells from the same species as the patient.

15. A method according to claim 13 comprising the further steps of covering the genetically engineered stem cells with a chamber having an opening securable at the periphery to the skin of the patient and being formed of a flexible, moisture and gas impermeable material and sealing the periphery of the chamber to the skin of the patient.

16. A method for genetically engineering cells in a patient, comprising
    attaching to the surface of the patient and at a site where cells are to be engineered a chamber formed of a flexible, moisture and gas impermeable material, the chamber containing a fluid medium suitable for culturing cells and open to the cells to be engineered, and
    introducing genetic material into the cells covered by the chamber.

17. The method of claim 16 wherein the cells are keratinocytes.

18. The method of claim 16 wherein the genetic material is introduced into the cells using a vector selected from the group consisting of viral vectors and plasmids.

19. The method of claim 16 wherein genetic material is introduced into the cells, further comprising controlling temperature, pH, growth of microorganisms, gas and ion concentrations.

20. The method of claim 16 further comprising providing in the chamber compounds selected from the group consisting of antibiotics, anesthetics, chemotherapeutic agents, immunomodulators, and growth factors.

21. A method for increasing the yield of genetically engineered cells implanted in a patient, comprising the steps of selecting epidermal stem cells as the cells to be engineered, covering the implanted stem cells with a chamber, and introducing genetic material to the cells within said chamber, said chamber having an opening securable at the periphery to the skin of the patient and being formed of a flexible, moisture and gas impermeable material wherein said chamber contains the genetic material and the cells to be genetically engineered.

22. A method according to claim 21 wherein the step of selecting epidermal stem cells includes the step of exposing the basal layer of the patient's epidermis for the stem cells.

* * * * *